United States Patent [19]

Hirsch

[11] 4,061,663
[45] Dec. 6, 1977

[54] PROCESS FOR PREPARATION OF ALIPHATIC PRIMARY SULFAMATES

[75] Inventor: Allen Frederick Hirsch, Somerville, N.J.

[73] Assignee: Ortho Pharmaceutical Corporation, Raritan, N.J.

[21] Appl. No.: 618,998

[22] Filed: Oct. 2, 1975

[51] Int. Cl.² ............................................. C07C 143/68
[52] U.S. Cl. ................................. 260/456 A; 424/303
[58] Field of Search ...................................... 260/456 A

[56] References Cited

U.S. PATENT DOCUMENTS 2,839,562  6/1958  Wegler et al. .................... 260/456 A
3,898,262  8/1975  Fischer et al. .................... 260/456 A

OTHER PUBLICATIONS

Catt et al. J. Org. Chem., 39,566 (1974).
Barton, "Protective Groups in Org. Chem.," pp. 61–64 (1973).

Primary Examiner—Nicky Chan
Attorney, Agent, or Firm—Benjamin F. Lambert

[57] ABSTRACT

Aliphatic primary sulfamates are prepared by reacting an alkanediol with a substituted sulfamoyl halide containing a protecting group which can be readily removed under acid conditions. The aliphatic primary sulfamates are useful in the control of fertility in male animals.

9 Claims, No Drawings

PROCESS FOR PREPARATION OF ALIPHATIC PRIMARY SULFAMATES

BACKGROUND OF THE INVENTION

The present invention relates to a process for the preparation of aliphatic primary sulfamates. The sulfamates which can be prepared by the present process may be represented by the formula:

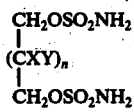

wherein $n$ is an integer from 0–8 and X and Y are hydrogen, provided that when $n$ is 1, X and Y are either hydrogen, lower alkyl having 1–3 carbon atoms, aryl such as phenyl or arylalkyl such as benzyl, phenethyl and the like.

The aliphatic primary sulfamates of the present invention are prepared by reacting an alkanediol with a substituted sulfamoyl halide such as a substituted sulfamoyl chloride, for example, in a suitable solvent in the presence of a strong base. Suitable alkanediols which may be employed include 1,2-ethanediol, 1,3-propanediol, 1,4-butanediol, 1,5-pentanediol, 1,10-decanediol and the like. As the halide reactant, a substituted sulfamoyl halide is employed wherein the substituent is a protecting group which can be readily removed under acid conditions. Suitable groups which may be employed include groups such as t-butyl, benzyl, α-alkyl benzyl wherein the alkyl group has 1–3 carbon atoms, allyl and 1-alkyl-allyl wherein the alkyl group has 1–3 carbon atoms. The substituent on the sulfamoyl halide reactant is removed by treating the compound obtained from the reaction mixture with a strong acid. Acids such as trichloroacetic acid, trifluoroacetic acid, methanesulfonic acid, conc. sulfuric acid and conc. hydrochloric acid, for example, may be employed. The preparation of unsubstituted sulfamoyl halides involves steps which are inherently hazardous. The use of a substituted sulfamoyl halide in place of an unsubstituted sulfamoyl halide avoids the hazards associated with the preparation of sulfamoyl halides. Substituted sulfamoyl halides are prepared by reacting an appropriate amine such as, for example, t-butylamine or benzylamine, with a sulfuryl halide in a suitable solvent, such as acetonitrile, for example. Bases such as sodium hydride, potassium t-butoxide, potassium hydride, tributyltin, sodium amide and sodium are examples of bases which may be employed for the initial reaction. Suitable solvents for the reaction include toluene, benzene, xylene, ether, tetrahydrofuran, diglyme, 1,2-dimethoxyethane and p-dioxane.

The reaction with the substituted sulfamoyl halide may be carried out at room temperature, but it is preferred to carry out the reaction at a temperature between room temperature and about 60° C. The removal of the protecting group is preferably carried out at room temperature in an inert atmosphere such as nitrogen, for example. The product is obtained from the reaction mixture by techniques known to those skilled in the art.

The aliphatic primary sulfamates, which are the subject of this invention, are useful in the control of fertility in male animals. The compounds are capable of interfering with sperm as they sojourn in the epididymis and thus bring about what is known as functional sterility, i.e., the gametes remain morphologically normal and show motility but normal fertilization is not achieved. Generally dosage levels of from about 5–200 mg./kg. are effective in inducing functional sterility. The preferred dosage range is from about 10–150 mg/kg. In addition to causing functional sterility of epididymal sperm, the primary sulfamates have antiandrogenic properties as manifested by inhibition of the size of the ventral prostate.

The general procedure followed to determine the activity of compounds which inhibit male fertility by altering the functional capacity of epididymal sperm is as follows:

A two week dosing period (i.e, the approximate period required for sperm transport through the epididymis) enables the separation of those drugs which affect epididymal sperm maturation and/or function from the antispermatogenic agents which have a longer delay in the onset of sterility. Each individual test involves 5 male rats (250–300 g.) caged together in air conditioned animal quarters and maintained on laboratory chow and tap water ad libitum. The compound to be tested is dissolved or suspended in appropriate vehicles (usually methylcellulose) and administered daily (usually i.g.) for 14 consecutive days. Control animals receive the vehicle only. At the end of the 14th day of treatment each male is individually caged with a proestrus female. Vaginal smears are checked the following morning for evidence of positive mating, and those males failing to mate are recohabited with proestrus females the following night. Males are sacrificed and autopsied the day after cohabitation for a gross examination of testes, epididymides, and accessory sex organs. Tissue samples of these organs are preserved for histological processing if observation yields a possible effect. Feamles (regardless of sperm presence in the vaginal washings) are autopsied 14 days after cohabitation to examine for pregnancy.

The inability of females to produce a viable embryo following a successful mating with treated males (two weeks of medication) is used as a measure of functional infertility. The number of males mating of those cohabited gives a gross indication of the drug's effect on libido. The size of the accessory sex organs provides an indication of the effect on androgen production. Microscopic analysis of epididymal sperm provides information on sperm quality (motility and morphology) and quantity.

The following examples describe the invention in greater particularity and are intended to be a way of illustrating and not limiting the invention.

EXAMPLE 1

1,2-Bis-O-sulfamyl-1,2-ethanediol

Ethylene glycol (21.7 ml., 0.385 mol.) is added dropwise during 15 mins to a suspension of sodium hydride (37 g. 50% m.o., 0.77 mol.) in toluene (450 ml.) at room temperature. The suspension is stirred for 15 mins., then warmed slowly to 45°14 50° C and stirred at that temperature for 2.5 hrs. The reaction mixture is then cooled to 20° C and a solution of t-butyl-sulfamoyl chloride (132 g., 0.77 mol.) in toluene (131 ml.) is added dropwise at 20°–35° C during 1.25 hrs. Heavy foaming occurs during the addition, and cooling is required to maintain the temperature at 20°–35° C. The resulting tan colored viscous suspension is stirred for 2.5 hrs. at 20° C, then for 1.5 hrs. at 45°–50° C and then for 16 hrs. without further heating. The gelatinous solid which forms is collected by filtration, washed with toluene, and extracted twice with hot chloroform (600 ml., 300 ml.). The solids which remain are then suspended in water (500 ml.) and extracted with chloroform until no solid remains. The chloroform extracts are combined and evaporated. The resulting solid is crystallized from chloroform/heptane to afford 72.26 g. (56.4%) of 1,2-bis-O-(N-t-butylsulfamyl)-1,2-ethanediol, m.p. 119°–121°. The crystalline compound (110 g., 0.33 mol.) is added to $CF_3CO_2H$ (330 ml.) with stirring at 25° under $N_2$. The resulting clear solution is stirred at room temperature for 20 hrs. The solid is collected by filtration, washed with $CHCl_3$ (2 × 50 ml.) and dried in vacuo at 50°–55° to afford the crude product (61.1 g. 84%). The crude material (61.1 g.) is dissolved in acetone (185 ml.) at reflux temperature and treated with charcoal (1.2 g.). The charcoal suspension is refluxed for 5 mins. and then filtered through Supercel. The colorless filtrate is treated with $CHCl_3$ (185 ml.), cooled and stirred at 0°–5° for 1 hr. The solid which settles out is collected by filtration and dried in vacuo at 50°–55° to afford 54.0 g. (75.5%) of 1,2-bis-O-sulfamyl-1,2-ethanediol, m.p. 98.5°–101°.

EXAMPLE 2

1,10-Bis-O-sulfamyl-1,10-decanediol 1,10-Bis-O-sulfamyl-1,10-decanediol is prepared in the same manner as 1,2-bis-O-sulfamyl-1,2-ethanediol in Example 1 except that 1,10-decanediol (67 g., 0.385 mol.) is employed as the alkanediol.

When in the above procedure 1,6-hexanediol is employed in place of 1,10-decanediol, 1,6-bis-O-sulfamyl-1,6-hexanediol is obtained

EXAMPLE 3

1,4-Bis-O-sulfamyl-1,4-butanediol 1,4-Bis-O-sulfamyl-1,4-butanediol is prepared in the same manner as 1,2-bis-O-sulfamyl-1,2-ethanediol in Example 1 except that 1,4-butanediol (34.6 g., 0.385 mol.) is employed as the alkanediol.

When in the above procedure 1,7-heptanediol is employed in place of 1,4-butanediol, 1,7-bis-O-sulfamyl-1,7heptanediol is obtained.

EXAMPLE 4

1,3-Bis-O-sulfamyl-1,3-propanediol 1,3-Bis-O-sulfamyl-1,3-propanediol is prepared in the same manner as 1,2-bis-O-sulfamyl-1,2-ethanediol in Example 1 except that 1,3-propanediol (29.2 g., 0.385 mol.) is employed as the alkanediol.

When in the above procedure 1,8-octanediol and 1,9-nonanediol are employed in place of 1,3-propanediol, 1,8-bis-O-sulfamyl-1,8-octanediol and 1,9-bis-O-sulfamyl-1,9-nonanediol, respectively, are obtained.

EXAMPLE 5

2-Methyl-2-propyl-1,3-bis-O-sulfamyl-1,3-propanediol

2-Methyl-2-propyl-1,3-bis-O-sulfamyl-1,3-propanediol is prepared in the same manner as 1,2-bis-O-sulfamyl-1,2-ethanediol in Example 1 except that 2-methyl-2-propyl-1,3-propanediol (50.8 g., 0.385 mol.) is employed as the alkanediol.

When in the above procedure 2-ethyl-2-propyl-1,3-propanediol, 2,2-dimethyl-1,3 -propanediol and 2-methyl-yl-1,3-propanediol are employed instead of 2-methyl-2-propyl-1,3-propanediol, 2-ethyl-2-propyl-1,3-bis-O-sulfamyl-1,3-propanediol, 2,2-dimethyl-1,3-bis-O-sulfamyl-1,3-propanediol and 2-methyl-1,3-bis-O-sulfamyl-1,3-propanediol, respectively, are obtained.

EXAMPLE 6

2,2-Diphenyl-1,3-bis-O-sulfamyl-1,3-propanediol 2,2-Diphenyl-1,3-bis-O-sulfamyl-1,3-propanediol is prepared in an identical manner as the sulfamate reported in Example 1 except for the use of 2,2-diphenyl-1,3-propanediol (87.7 g., 0.385 mol.) as the alkanediol.

When in the above procedure 2,2-dibenzyl-1,3-propanediol and 2,2-dicyclohexyl-1,3-propanediol are employed in place of 2,2-diphenyl-1,3-propanediol, 2,2-dibenzyl-1,3-bis-O-sulfamyl-1,3-propanediol and 2,2-dicyclohexyl-1,3-bis-O-sulfamyl-1,3-propanediol are obtained.

Preparation of t-butyl-sulfamoyl chloride

T-Butylamine (65.7 g., 0.90 mol.) is added during 1 hr. at 20°–30° C to a stirred solution of sulfuryl chloride (240 ml., 3 mol.) in acetonitrile (450 ml.). A vigorous evolution of hydrogen chloride takes place and the amine hydrochloride settles out of solution. The mixture is refluxed for 24 hrs. and additional sulfuryl chloride (240 ml.) is added. After stirring and refluxing the mixture for 40 hrs., a more complete solution forms. The solution is concentrated in vacuo to a viscous oil which is distilled under reduced pressure. A main fraction is collected at 89°–94° C. 0.3–0.5 mm., 100.1 g., 64.8% yield. On standing, transparent, needle-like crystals of t-butyl-sulfamoyl chloride form, m.p. 28°–30° C.

What is claimed is:

1. The process for the preparation of a compound of the formula:

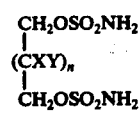

which comprises reacting an alkanediol of the formula:

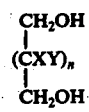

with a substituted sulfamoyl halide of the formula:

in the presence of a base and treating the resulting intermediate compound with a strong acid, wherein n is an integer from 0–8 and X and Y are hydrogen, provided that when n is 1, X and Y are hydrogen, lower alkyl having 1–3 carbon atoms, phenyl and benzyl and phenethyl, R is a protecting group capable of being removed by strong acid at a temperature between room temperature and 60° C, wherein the strong acid is selected from trichloroacetic acid, trifluoroacetic acid, methanesulfonic acid, sulfuric acid, and hydrochloric acid and the protecting group is selected from the group consisting of t-butyl, benzyl, α-alkyl benzyl wherein the alkyl group has 1–3 carbon atoms, allyl and 1-alkyl-allyl wherein the alkyl group has 1-3 carbon atoms, and M is a halogen.

2. The process of claim 1 wherein the substituted sulfamoyl halide is t-butylsulfamoyl chloride.

3. The process of claim 1 wherein the acid is trifluoroacetic acid.

4. The process of claim 1 wherein the base is sodium hydride.

5. The process of claim 1 wherein $n$ is 0.

6. The process of claim 1 wherein $n$ is 1 and X and Y are hydrogen.

7. The process of claim 1 wherein $n$ is 2 and X and Y are hydrogen.

8. The process of claim 1 wherein $n$ is 8 and X and Y are hydrogen.

9. The process of claim 1 wherein $n$ is 1, X is methyl and Y is ethyl.

* * * * *

UNITED STATES PATENT AND TRADEMARK OFFICE
CERTIFICATE OF CORRECTION

PATENT NO. : 4,061,663
DATED : Dec. 6, 1977
INVENTOR(S) : Hirsch

It is certified that error appears in the above-identified patent and that said Letters Patent are hereby corrected as shown below:

In Column 1, line 32, "t-butyl" should read "$\underline{t}$-butyl"
In Column 1, line 47, "t-butylamine" should read "$\underline{t}$-butylamine"
In Column 1, line 50, "t-butoxide" should read "$\underline{t}$-butoxide"
In Column 1, line 55, "p-dioxane" should read "$\underline{p}$-dioxane"
In Column 2, line 23, "ad libitum" should read "$\underline{ad\ libitum}$"
In Colmun 2, line 37, "Feamles" should read "Females"
In Column 2, line 55, "Bis" should be underscored
In Column 2, line 61, "45°14 50°C" should read "45-50°C"
In Column 2, line 63, "t-butyl" should read "$\underline{t}$-butyl"
In Column 3, line 10, "bis" and "t" should be underscored
In Column 3, line 15, "in vacuo" should be underscored
In Column 3, line 23, "in vacuo" should be underscored
In Column 3, lines 24,27,28,30,34, "bis" should be underscored
In Column 3, line 34, "of1" should read "of 1"
In Column 3, lines 39,40,41,44 "bis" should be underscored
In Column 3, line 45, "1,7heptanediol" should read "1,7-heptanediol"
In Column 3, lines 49,50,51,56,57,60,61,62, "bis" should be underscored
In Column 4, lines 2,3,4,9,10,17,18, "bis" should be underscored
In Column 4, line 20, "t-butyl" should read "$\underline{t}$-butyl"
In Column 4, line 21, "T-Butylamine" should read "$\underline{T}$-Butylamine"
In Column 4, line 30, "in vacuo" should be underscored
In Column 4, line 34, "t-butyl " should read "$\underline{t}$-butyl"

UNITED STATES PATENT AND TRADEMARK OFFICE
CERTIFICATE OF CORRECTION

PATENT NO. : 4,061,663
DATED : Dec. 6, 1977
INVENTOR(S) : Hirsch

It is certified that error appears in the above-identified patent and that said Letters Patent are hereby corrected as shown below:

In Column 4, line 67, "t-butyl" should read "*t*-butyl"
In Column 5, line 4, "t-butylsulfamoyl" should read "*t*-butylsulfamoyl"

Signed and Sealed this

Eighth Day of August 1978

[SEAL]

Attest:

RUTH C. MASON
Attesting Officer

DONALD W. BANNER
Commissioner of Patents and Trademarks